(12) United States Patent
Falck et al.

(10) Patent No.: US 7,084,281 B2
(45) Date of Patent: Aug. 1, 2006

(54) SYNTHESIS OF DIHALOHYDRINS AND TRI- AND TETRA-SUBSTITUTED OLEFINS

(75) Inventors: John R. Falck, Dallas, TX (US); Deb K. Barma, Dallas, TX (US); Abhijit Kundu, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 555 days.

(21) Appl. No.: 10/349,199

(22) Filed: Jan. 22, 2003

(65) Prior Publication Data

US 2004/0143125 A1 Jul. 22, 2004

(51) Int. Cl.
*C07D 209/18* (2006.01)
*C07D 317/44* (2006.01)
*C07C 229/00* (2006.01)
*C07C 69/76* (2006.01)
*C07C 69/74* (2006.01)

(52) U.S. Cl. .................. 548/502; 549/438; 560/47; 560/104; 560/128

(58) Field of Classification Search .................... None
See application file for complete search history.

(56) References Cited

OTHER PUBLICATIONS

Knochel et al, Tetrahedron, Preparation and Reactivity of Functionalized Alkenyl-Zinc, -Copper, and -Chromium Organometallics, 1993, 49(1), pp. 29-48.*
Okazoe et al, Journal of the American Chemical Society, (E)-Selective Olefination of Aldehydes by Means of gem-Dichromium Reagents Derived by Reduction of gem-Diiodoalkanes with Chromium(II) Chloride, 1987, 109, pp. 951 and 953.*

\* cited by examiner

*Primary Examiner*—Paul A. Zucker
(74) *Attorney, Agent, or Firm*—Jackson Walker L.L.P.

(57) ABSTRACT

A novel synthesis reaction for highly stereospecific tri- and tetra-substituted olefins is described. A single stereoisomer of stable α-halo-α,β-ester is produced in high yield by the reaction of aldehyde or ketone with a trihalogenated compound such as trichloroacetate in the presence of $CrCl_2$ in a solvent. By varying the amount of $CrCl_2$ used, the stable dihalohydrin intermediate may be obtained as well.

33 Claims, No Drawings

SYNTHESIS OF DIHALOHYDRINS AND TRI- AND TETRA-SUBSTITUTED OLEFINS

BACKGROUND

One embodiment of this invention relates to synthesis of olefins and, in particular, to stereospecific synthesis of tri- and tetra-substituted olefins.

The highly stereoselective construction of tri- and tetra-substituted olefins is currently one of the most challenging problems in synthetic organic chemistry. Tri- and tetra-substituted olefins are common structural units in almost every class of compounds, particularly natural products. Their synthesis is consequently of great importance to the pharmaceutical, agricultural, and fine chemical industries. However, there are few methods that can do this efficiently, economically, and with high stereoselectivity. Many extant procedures give poor yields, require expensive reagents, have inconvenient reaction conditions, produce undesirable by-products, and afford mixtures of isomers. Since the isomers and by-products may be hard to remove, impart undesirable chemical or physical properties, and have unwanted biological properties, these compounds must be separated by methods that can be costly, difficult to conduct on a large scale, and time consuming.

The literature provides some examples of methods for the synthesis of tri-substituted olefins. (See Tago et al., *Organic Lett.*, 2:1975–78 (2000); Ishino et al., *Bull. Chem. Soc. Jpn.*, 71:2669–72 (1998); Goumain et al., *Synthesis*, 6:984 (1999); and Kruper et al., *J. Org. Chem.*, 56:3323–29 (1991)). In addition, some previous examples exist for the synthesis of tetra-substituted olefins, such as α-halo acrylates. (See Takai et al., *Bull. Chem. Soc. Jpn.*, 53:1698–1702 (1980); Masahira et al., *Synth. Commun.*, 30:863–68 (2000); Terent'ev et al., *Russ. Chem. Bull.*, 48:1121–27 (1999)). However, these methods tend to be inefficient due to lack of stereoselectivity or the need for a multi-step procedure.

Most frequently, Wittig and Horner-Wadsworth-Emmons ("HWE") reactions are used in the synthesis of various olefins. (See Wadsworth et al., *Org. React.*, 25:73 (1977); Maryanoff et al., *Chem. Rev.*, 89:863 (1989); and Vedejs et al., *Top. Stereochem.*, 21:1 (1994)). But the construction of tri- and tetra-substituted alkenes is subject to the limitations of variable stereoselectivity, costly reagents, and low yields.

SUMMARY

One aspect of the current invention relates to an efficient synthesis method for the stereoselective production of tri- and tetra-substituted olefins in high yield. A single stereoisomer of (Z)-α-halo-α,β-unsaturated ester, also known as α-halo-(Z)-acrylate, is produced in a reaction between aldehydes and trihalogenated compounds such as trichloroacetate. Aldehydes in combination with dihalogenated propionates, as well as higher homologs of the dihalogenated propionates with longer carbon chains, also produce stereospecific results. These reactions are carried out in the presence of a reductant, such as 4 $CrCl_2$ or catalytic $CrCl_2$, Mn, and chlorotrimethylsilane ("TMSCl") in a polar solvent, preferably at ambient temperatures and under an inert atmosphere, such as an argon or nitrogen atmosphere. The same method produces tetra-substituted olefins of good stereoselectivity if ketones are used instead of aldehydes. Solvents that can be used for these reactions include tetrahydrofuran ("THF"), dimethylformamide ("DMF"), ethylene glycol dimethyl ether ("DME"), other polar solvents, and a mixture thereof.

In addition, using 2 equivalents of $CrCl_2$ rather than 4 produces the intermediate dihalohydrin compound in very high yield. Further conversion of the dihalohydrin to principally one stereoisomer of tri- or tetra-substituted olefin is possible by adding another 2 equivalents of $CrCl_2$. Thus, in a single step, by varying the amount of $CrCl_2$, the final product may be either the olefin or the dihalohydrin. The general scheme for this reaction is illustrated below. In this reaction scheme, X may be Cl, Br, F, an alkyl group, or an aryl group. R and R' may be similar or different and may be alkyl, allyl, aryl, heteroaryl, aliphatic, or cycloaliphatic groups. The trihalogenated compound is illustrated as 1, the intermediate dihalohydrin is 2, and the substituted olefin is 3.

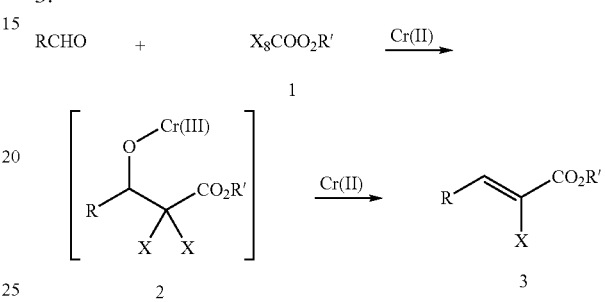

As an example, remarkably high stereoselectivities are observed when acetophenone and methyl trichloroacetate are used to produce the tetra-substituted olefin in a 75:1 Z/E ratio. In another variation, the transformation of aldehyde to (E)-methacrylate using 2,2-dichloropropionate is unrivaled by conventional reagents for its stereoselectivity (greater than 99% of the (E)-isomer) and yield.

Although not wanting to be bound by theory, it is likely that the reaction mechanism involves the oxidative addition of Cr(II) into a C—Cl bond via two consecutive single electron transfers and subsequent addition to the aldehyde carbonyl. Subsequent E2-elimination of the resultant Reformatsky-type adduct 2 affords the α-haloacrylate 3. Of the possible anti-periplanar conformations illustrated below, conformer A is favored because it minimizes the steric interactions between the ester and R group. Selective metallation of the chloride furthest from the chromate ester ensures the observed stereochemistry.

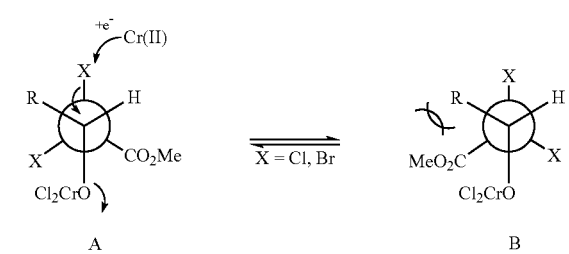

The synthesis of (Z)-halogenated tri- and tetra-substituted olefins is useful in the synthesis of various biologically active products by the method of transition metal mediated cross-coupling. Applications range from the preparation of α-amino acids, heterocycles, polymers, and aziridines to natural products and pharmaceuticals.

DETAILED DESCRIPTION OF PREFERRED EMBODIMENTS

The results from a panel of representative substrates in the synthesis of tri-substituted olefins, or α-haloacrylates are summarized in Table 1 below.

TABLE 1

Synthesis of (Z)-α-Haloacrylates

| Entry | Aldehyde | Acrylate | | |
|---|---|---|---|---|
| 1 | PhCH$_2$CH$_2$CHO | Ph(CH$_2$)$_2$CH=C(X)CO$_2$R | | |
| | | X=Cl, R = Me | | 99 |
| | | X = F, R = Et | | 98 |
| 2 | PhCH(CH$_3$)CHO | PhCH(CH$_3$)CH=C(Cl)CO$_2$Me | | 99 |
| 3 | 2,2-dimethyl-1,3-dioxolan-4-yl-CHO | 2,2-dimethyl-1,3-dioxolan-4-yl-CH=C(Cl)CO$_2$Me | | 99 |
| 4 | PhCHO | PhCH=C(Cl)CO$_2$Me | | 100 |
| 5 | PhCH=CHCHO | PhCH=CH-CH=C(Cl)CO$_2$Me | | 99 |
| 6 | 4-F$_3$C-C$_6$H$_4$-CHO | 4-F$_3$C-C$_6$H$_4$-CH=C(Cl)CO$_2$Me | | 98 |
| 7 | 4-H$_3$CO-C$_6$H$_4$-CHO | 4-H$_3$CO-C$_6$H$_4$-CH=C(X)CO$_2$R | | |
| | | X = Cl, R = Me | | 98 |
| | | X = Br, R = Me | | 98 |
| | | X = F, R = Et | | 98 |
| 8 | 3-H$_3$CO-4-BnO-C$_6$H$_3$-CHO | 3-H$_3$CO-4-BnO-C$_6$H$_3$-CH=C(Cl)CO$_2$Me | | 99 |
| 9 | 3-Br-C$_6$H$_4$-CHO | 3-Br-C$_6$H$_4$-CH=C(Cl)CO$_2$Me | | 99 |
| 10 | 3,4-methylenedioxy-C$_6$H$_3$-CHO | 3,4-methylenedioxy-C$_6$H$_3$-CH=C(X)CO$_2$Me | | |
| | | X = Cl | | 99 |
| | | X = Br | | 98 |

TABLE 1-continued

Synthesis of (Z)-α-Haloacrylates

| Entry | Aldehyde | Acrylate | |
|---|---|---|---|
| 11 | 4-(dimethylamino)benzaldehyde | methyl (Z)-2-chloro-3-(4-(dimethylamino)phenyl)acrylate | 98 |
| 12 | indole-3-carboxaldehyde | methyl (Z)-2-chloro-3-(1H-indol-3-yl)acrylate | 91[a] |

[a]Required 8 equiv of $CrCl_2$

Specifically, aliphatic aldehyde or secondary aldehyde, stirred with 4 equivalents of commercial $CrCl_2$ and methyl trichloroacetate at room temperature for 0.5 hours generates the corresponding (Z)-α-halo-α,β-unsaturated ester products shown in Table 1 under entries 1 and 2 respectively. Nuclear magnetic resonance ("NMR") analysis of the crude reaction mixture does not detect any of the (E)-isomer, indicating better than 99% stereochemical purity. A catalytic $CrCl_2$ system, utilizing Mn powder to recycle chromium (III) to chromium (II), also produces a good yield of the desired products.

Illustrated in entries 3, 4, and 5 respectively, condensation of chiral carboxaldehyde, simple benzaldehyde, and cinnamaldehyde produces corresponding tri-substituted olefin compounds in high yield. Furthermore, neither the reaction rate nor yield are significantly influenced by electron donating or withdrawing substituents on the substrates, as shown in entries 7 and 10. The resulting products were present in high yield. The reaction is compatible with a variety of functional groups, including reactive bromine (entry 9), benzyloxy (entry 8), bis-methyleneoxy ether (entry 10), tertiary amine (entry 11) and secondary amine (entry 12). The transformation also proceeds smoothly with methyl tribromoacetate and p-anisaldehyde (entry 7, where X=Br and R=Me). All reaction products are present in high yield.

The standard stoichiometric reaction also works well for the synthesis of tetra-substituted olefins. Reacting methyl trihaloacetate with ketones gives good yield of the tetra-substituted halo esters in about a 1:5 ratio of (E) to (Z)-stereoisomers, but this ratio varies depending on the substrate. By isolating the alcohol product first by using 2 equivalents of $CrCl_2$, then treating with an additional 2 equivalents of $CrCl_2$, the stereochemical ratio may be increased up to 1:16 with some substrates. As a generalized illustration of the tetra-substituted synthetic methodology, results from reactions with different substrates are shown in Table 2 below. The synthesized tetra-substituted olefins, or adducts, are illustrated.

TABLE 2

Olefination of ketones

| Entry | Ketone | Adduct | Yield (%) | E/Z |
|---|---|---|---|---|
| 1 | 2-heptanone derivative | chloro methyl acrylate adduct | 95 | 1/2.5 |
| 2 | acetophenone | methyl (Z)-2-chloro-3-phenylbut-2-enoate | 98 | 1/5[a] |
| 3 | 1-(cyclohex-1-en-1-yl)ethanone | methyl 2-chloro-3-(cyclohex-1-en-1-yl)but-2-enoate | 95 | 1/2.5 |

TABLE 2-continued

Olefination of ketones

| Entry | Ketone | Adduct | Yield (%) | E/Z |
|---|---|---|---|---|
| 4 | (cyclohexenyl methyl vinyl ketone structure) | (chloro methyl ester diene adduct structure) | 93 | 1/5 |

[a] Z/E 75:1 in THF/DMF (1:1)

As shown in entries 1, 2, 3, and 4 respectively, aliphatic ketone, aromatic ketone, conjugated ketone, and hindered ketone give rise to reaction products in excellent yield after the addition of methyl trihaloacetate. The tetra-substituted olefin of Entry 2 was synthesized at a Z/E ratio of 75:1 when the solvent used was a mixture of THF and DMF in equal parts, while the Z/E ratio of 5:1 was obtained in THF alone.

Using 2 equivalents of $CrCl_2$ at a reaction temperature of about 0° C., rather than 2 equivalents of $CrCl_2$ at about room temperature, allows the isolation of the intermediate dihalohydrin compounds in moderate to good yield as well. The results from a panel of representative substrates in the synthesis of dihalohydrins, or adducts, are summarized in Table 3 below.

TABLE 3

Synthesis of dihalohydrin

| Entry | Aldehyde | Adduct | Yield (%) |
|---|---|---|---|
| 1 | PhCHO | Ph-CH(OH)-C(Cl)₂-CO₂Me | 82 |
| 2 | PhCHO | Ph-CH(OH)-C(Br)₂-CO₂Me | 65 |
| 3 | PhCH₂CH₂CHO | PhCH₂CH₂-CH(OH)-C(Cl)₂-CO₂Me | 84 |
| 4 | PhCH=CH-CHO | PhCH=CH-CH(OH)-C(Cl)₂-CO₂Me | 78 |
| 5 | (dimethyl dioxolane-CHO) | (dimethyl dioxolane-CH(OH)-C(Cl)₂-CO₂Me) (d.e. 1:1.4) | 75 |

TABLE 3-continued

Synthesis of dihalohydrin

| Entry | Aldehyde | Adduct | Yield (%) |
|---|---|---|---|
| 6 | PhCH₂CH₂-CHO | Ph-CH₂CH₂-CH(OH)-CF₂-CO₂Et | 76 |

A variety of trihalogenated compounds, in addition to trichloroacetate, may be used to synthesize the substituted olefins, or adducts. As illustrated below in Table 4, these trihalogenated compounds include 2,2,2-trichloroacetamide (entries 1–2), 1,1,1-trichlorotoluene (entries 3–4), and 1,1,1-trichloroacetone (entries 5–6). In addition, entries 7 and 8 show the formation of substituted olefins in good yield with the use of α,α-dichloropropiophenone.

TABLE 4

Olefinations using other trihalogenated compounds

| Entry | Aldehyde | Chloride | Adduct | Yield (%) |
|---|---|---|---|---|
| 1 | Ph-CHO | Cl₃C-C(O)-NH₂ | Ph-CH=C(Cl)-C(O)-NH₂ | 95 |
| 2 | Ph-CH₂CH₂-CHO | Cl₃C-C(O)-NH₂ | Ph-CH₂CH₂-CH=C(Cl)-C(O)-NH₂ | 92 |
| 3 | Ph-CHO | Cl₃C-Ph | Ph-CH=C(Cl)-Ph | 95 |
| 4 | Ph-CH₂CH₂-CHO | Cl₃C-Ph | Ph-CH₂CH₂-CH=C(Cl)-Ph | 93 |
| 5 | Ph-CHO | Cl₃C-C(O)-CH₃ | Ph-CH=C(Cl)-C(O)-CH₃ | 99 |
| 6 | Ph-CH₂CH₂-CHO | Cl₃C-C(O)-CH₃ | Ph-CH₂CH₂-CH=C(Cl)-C(O)-CH₃ | 99 |

TABLE 4-continued

Olefinations using other trihalogenated compounds

| Entry | Aldehyde | Chloride | Adduct | Yield (%) |
|---|---|---|---|---|
| 7 | Ph-CHO | Cl₂C(Me)-C(O)- (naphthyl structure) | α-methyl enone adduct | 88 |
| 8 | Ph-CH₂-CHO | Cl₂C(Me)-C(O)- (naphthyl structure) | α-methyl enone adduct with CH₂CH₂ linker | 85 |

EXAMPLE 1

General Synthesis of Tri-substituted Olefins

Methyl trihaloacetate (1 mmol) and aldehyde (1 mmol) in THF (2 mL) were added to a stirring suspension of anhydrous $CrCl_2$ (4.5 mmol) in THF (8 mL) under argon at ambient temperature. After 0.5 hours, the resultant reddish reaction mixture was quenched with water, extracted three times with ether, and the combined ethereal extracts were evaporated in vacuo. Chromatographic purification on SiO2 resulted in (Z)-α-halo-α,β-unsaturated esters in the yields indicated in Table 1.

EXAMPLE 2

General Synthesis of Tri-substituted Olefins Using Catalytic Chromium

Methyl trihaloacetate (1 mmol) and aldehyde (1 mmol) in THF (2 mL) were added to a stirring suspension of anhydrous $CrCl_2$ (50 mol %), Mn power (4 mmol) and TMSCl (6 mmol) in THF (8 mL) under argon at ambient temperature. After 12 hours, the resultant reddish reaction mixture was quenched with water, extracted three times with ether, and the combined ethereal extracts were evaporated in vacuo. Chromatographic purification on $SiO_2$ resulted in (Z)-α-halo-α,β-unsaturated esters in yields comparable to those indicated in Table 1.

EXAMPLE 3

General Synthesis of Tetra-substituted Olefins

Methyl trihaloacetate (1 mmol) and ketone (1 mmol) in THF (2 mL) were added to a stirring suspension of anhydrous $CrCl_2$ (6 mmol) in THF (8 mL) under argon at ambient temperature. After 2 hours, the resultant reddish reaction mixture was quenched with water, extracted three times with ether, and the combined ethereal extracts were evaporated in vacuo. Chromatographic purification on $SiO_2$ resulted in (Z)-α-halo-α,β-unsaturated esters in the yields indicated in Table 2.

EXAMPLE 4

General Synthesis of Dihalohydrins

Methyl trihaloacetate (1 mmol) and aldehyde (1 mmol) in THF (2 mL) were added to a stirring suspension of anhydrous $CrCl_2$ (2.5 mmol) in THF (8 mL) under argon at 0° C. After 6 hours, the resultant reddish reaction mixture was quenched with water, extracted three times with ether, and the combined ethereal extracts were evaporated in vacuo. Chromatographic purification on $SiO_2$ gave the dihalohydrins, or adducts, shown in Table 3.

EXAMPLE 5

Synthesis of methyl 2-chloro-5-phenylpent-2(Z)-enoate

In accordance with the general procedure described in Example 1 above, ethyl dibromofluoroacetate and commercial hydrocinnamaldehyde were converted to methyl 2-chloro-5-phenylpent-2(Z)-enoate as an oil in the indicated yield for Entry 1, where X=Cl and R=Me, in Table 1.

$R_f$: 0.75 (15% EtOAc in hexane). $^1$H NMR ($CDCl_3$, 400 MHz): δ 2.64–2.72 (m, 2H,—$CH_2$—), 2.80 (t, 2H, J=7.6 Hz, Ph—$CH_2$—), 3.81 (s, 3H, $CO_2CH_3$), 7.01 (t, 1H, J=7.2 Hz), 7.18–7.26 (m, 3H), 7.28–7.34 (m, 2H). $^{13}$C NMR ($CDCl_3$, 75 MHz): δ 31.20, 33.83, 53.25, 125.23, 126.52, 128.49, 128.75, 140.65, 171.66, 163.11. MS: m/z 224 ($M^+$), 226 ($M^+$+2).

EXAMPLE 6

Synthesis of methyl 2-chloro-4-phenylpent-2(Z)-enoate

In accordance with the general procedure described in Example 1 above, commercial aliphatic branched aldehyde was converted to methyl 2-chloro-4-phenylpent-2(Z)-enoate as an oil in the indicated yield for Entry 2 in Table 1.

$R_f$: 0.70 (15% EtOAc in hexane). $^1$H NMR ($CDCl_3$, 300 MHz): δ 1.44 (d, 3H, J=6.6 Hz, $CH_3$), 3.81 (s, 3H, $CO_2CH_3$), 4.35–4.15 (m, 1H), 7.6 (d, 1H, J=9.6 Hz, CH═), 7.20–7.36 (m, 5H). $^{13}$C NMR ($CDCl_3$, 75 MHz): δ 20.10, 39.75, 53.29,

EXAMPLE 7

Synthesis of methyl 2-chloro-3-(2,2-dimethyl-[1,3]dioxolan-4(S)-yl)prop-2(Z)-enoate In accordance with the general procedure described in Example 1 above, chiral glyceraldehyde was converted to methyl 2-chloro-3-(2,2-dimethyl-[1,3]dioxolan-4(S)-yl)prop-2(Z)-enoate as an oil in the indicated yield for Entry 3 in Table 1.

$R_f$: 0.65 (15% EtOAc in hexane). $^1$H NMR (CDCl$_3$, 300 MHz): δ 1.41 (s, 3H, CH$_3$), 1.46 (s, 3H, CH$_3$), 3.71 (dd, 1H, J=6.6, 8.1 Hz), 3.85 (s, 3H, CO$_2$CH$_3$), 4.30 (dd, 1H, J=6.6, 8.4 Hz), 5.02 (dd, 1H, J=6.6, 13.5 Hz), 7.12 (d, 1H, 6.9 Hz). $^{13}$C NMR (CDCl$_3$, 75 MHz): δ 25.71, 26.60, 53.53, 68.40, 73.52, 110.44, 125.63, 140.81, 162.33. MS: m/z 220 (M$^+$), 222 (M$^+$+2).

EXAMPLE 8

Synthesis of methyl 2-chloro-3-phenyl-prop-2(Z)-enoate

In accordance with the general procedure described in Example 1 above, benzaldehyde was converted to methyl 2-chloro-3-phenyl-prop-2(Z)-enoate as an oil in the indicated yield for Entry 4 in Table 1.

$R_f$: 0.70 (15% EtOAc in hexane). $^1$H NMR (CDCl$_3$, 300 MHz): δ 3.89 (s, 3H, CO$_2$CH$_3$), 7.36–7.48 (m, 3H), 7.80–7.86 (m, 2H), 7.91 (s, 1H, Ph—CH=). $^{13}$C NMR (CDCl$_3$, 75 MHz): δ 53.55, 121.91, 128.72, 130.44, 130.83, 133.03, 137.42, 164.11. MS: m/z 196 (M$^+$), 198 (M$^+$+2).

EXAMPLE 9

Synthesis of methyl 2-chloro-5-phenylpent-2(Z),4(E)-dienoate

In accordance with the general procedure described in Example 1 above, commercial cinnamaldehyde was converted to methyl 2-chloro-5-phenylpent-2(Z),4(E)-dienoate as an oil in the indicated yield for Entry 5 in Table 1.

$R_f$: 0.72 (15% EtOAc in hexane). $^1$H NMR (CDCl$_3$, 300 MHz): δ 3.86 (s, 3H, CO$_2$CH$_3$), 7.00 (d, 1H, J=15.9 Hz), 7.19 (dd, 1H, J=10.8, 15.3 Hz), 7.30–7.40 (m, 3H), 7.46–7.54 (m, 2H), 7.62 (d, 1H, J=10.8 Hz). $^{13}$C NMR (CDCl$_3$, 75 MHz): δ 53.28, 122.3, 123.04, 127.73, 129.05, 129.74, 136.03, 138.23, 142.41, 163.67. MS: m/Z 222 (M$^+$), 224 (M$^+$+2).

EXAMPLE 10

Synthesis of methyl 2-chloro-3-(4-trifluoromethylphenyl)prop-2(Z)-enoate

In accordance with the general procedure described in Example 1 above, commercial p-trifluoromethylbenzaldehyde was converted to methyl 2-chloro-3-(4-trifluoromethylphenyl)prop-2(Z)-enoate as an oil in the indicated yield for Entry 6 in Table 1.

$R_f$: 0.73 (15% EtOAc in hexane). $^1$H NMR (CDCl$_3$, 300 MHz): δ 3.93 (s, 3H, CO$_2$CH$_3$), 7.68 (d, 2H, J=8.4 Hz), 7.91 (d, 2H, J=8.4 Hz), 7.93 (s, 1H). $^{13}$C NMR (CDCl$_3$, 75 MHz): δ 54.22, 124.84, 126.01, 126.11, 131.27, 136.17, 136.87, 164.04. MS: m/z 264 (M$^+$), 266 (M$^+$+2).

EXAMPLE 11

Synthesis of methyl 2-chloro-3-(4-methoxyphenyl)prop-2(Z)-enoate

In accordance with the general procedure described in Example 1 above, ethyl dibromofluoroacetate and commercial p-methoxybenzaldehyde were converted to methyl 2-chloro-3-(4-methoxyphenyl)prop-2(Z)-enoate as an oil in the indicated yield for Entry 7, where X=Cl and R=Me, in Table 1.

$R_f$: 0.68 (15% EtOAc in hexane). $^1$H NMR (CDCl$_3$, 300 MHz): δ 3.84 (s, 3H, CO$_2$CH$_3$), 3.88 (s, 3H,—OCH$_3$), 6.94 (d, 2H, J=8.7 Hz), 7.85 (d, 2H, J=8.7 Hz), 7.86 (s, 1H). $^{13}$C NMR (CDCl$_3$, 75 MHz): δ 53.41, 55.53, 114.18, 119.30, 125.70, 132.91, 137.00, 161.34, 164.41. MS: m/z 226 (M$^+$), 228 (M$^+$+2).

EXAMPLE 12

Synthesis of methyl 2-bromo-3-(4-methoxyphenyl)prop-2(Z)-enoate

In accordance with the general procedure described in Example 1 above, ethyl dibromofluoroacetate and commercial p-methoxybenzaldehyde were converted to methyl 2-bromo-3-(4-methoxyphenyl)prop-2(Z)-enoate as an oil in the indicated yield for Entry 7, where X=Br and R=Me, in Table 1.

$R_f$: 0.69 (15% EtOAc in hexane). $^1$H NMR (CDCl$_3$, 300 MHz): δ 3.84 (s, 3H, CO$_2$CH$_3$), 3.88 (s, 3H,—OCH$_3$), 6.94 (d, 2H, J=9.0 Hz), 7.90 (d, 2H, J=9.0 Hz), 8.17 (s, 1H). $^{13}$C NMR (CDCl$_3$, 75 MHz): δ 53.41, 55.53, 114.18, 119.30, 125.70, 132.91, 137.00, 161.34, 164.41. MS: m/z 226 (M$^+$), 228 (M$^+$+2).

EXAMPLE 13

Synthesis of methyl 2-chloro-3-(4-benzyloxy-3-methoxyphenyl)prop-2(Z)-enoate

In accordance with the general procedure described in Example 1 above, commercial 4-benzyloxy-3-methoxy-benzaldehyde was converted to methyl 2-chloro-3-(4-benzyloxy-3-methoxyphenyl)prop-2(Z)-enoate as an oil in the indicated yield for Entry 8 in Table 1.

$R_f$: 0.55 (15% EtOAc in hexane). $^1$H NMR (CDCl$_3$, 400 MHz): δ 3.89 (s, 3H,—CO$_2$CH$_3$), 3.93 (s, 3H,—OCH$_3$), 5.21 (s, 2H), 6.91 (d, 1H, J=8.4 Hz), 7.28–7.40 (m, 4H), 7.43 (d, 2H, J=7.2 Hz), 7.57 (s, 1H), 7.84 (s, 1H). $^{13}$C NMR (CDCl$_3$, 75 MHz): δ 53.46, 56.19, 70.92, 113.16, 113.73, 119.47, 125.42, 126.23, 127.37, 128.23, 128.84, 136.64, 137.15, 149.33, 150.23, 164.35. MS: m/z 332 (M$^+$), 334 (M$^+$+2).

EXAMPLE 14

Synthesis of methyl 2-chloro-3-(3-bromophenyl)prop-2(Z)-enoate

In accordance with the general procedure described in Example 1 above, commercial 3-bromo-benzaldehyde was converted to methyl 2-chloro-3-(3-bromophenyl)prop-2(Z)-enoate as an oil in the indicated yield for Entry 9 in Table 1.

R$_f$: 0.71 (15% EtOAc in hexane). $^1$H NMR (CDCl$_3$, 300 MHz): δ 3.91 (s, 3H, CO$_2$CH$_3$), 7.30 (t, 1H, J=7.80 Hz), 7.50–7.55 (m, 1H), 7.70–7.75 (m, 1H), 7.83 (s, 1H), 7.98 (t, 1H, J=1.8 Hz). $^{13}$C NMR (CDCl$_3$, 75 MHz): δ 53.70, 122.77, 123.40, 129.31, 130.21, 133.24, 133.30, 135.0, 135.76, 163.68. MS: m/z 274 (M$^+$), 276 (M$^+$+2).

EXAMPLE 15

Synthesis of methyl 2-chloro-3-(1,3-benzodioxol-5-yl)prop-2(Z)-enoate

In accordance with the general procedure described in Example 1 above, commercial benzaldehyde with a methylenedioxy group was converted to methyl 2-chloro-3-(1,3-benzodioxol-5-yl)prop-2(Z)-enoate as an oil in the indicated yield for Entry 10 in Table 1, where X=Cl.

R$_f$: 0.65 (15% EtOAc in hexane). $^1$H NMR (CDCl$_3$, 300 MHz): δ 3.89 (s, 3H, CO$_2$CH$_3$), 6.03 (s, 4H), 6.86 (d, 1H, J=8.4 Hz), 7.27 (dd, 1H, J=1.5, 7.2 Hz), 7.59 (d, 1H, J=1.8 Hz), 7.82 (s, 1H). MS: m/z 240 (M$^+$), 242 (M$^+$+2).

EXAMPLE 16

Synthesis of methyl 2-bromo-3-(1,3-benzodioxol-5-yl)prop-2(Z)-enoate

In accordance with the general procedure described in Example 1 above, commercial benzaldehyde with a methylenedioxy group was converted to methyl 2-bromo-3-(1,3-benzodioxol-5-yl)prop-2(Z)-enoate as an oil in the indicated yield for Entry 10 in Table 1, where X =Br.

R$_f$: 0.48 (15% EtOAc in hexane). $^1$H NMR (300 MHz) δ 3.89 (s, 3H), 6.03,(s, 2H), 6.85 (d, 1H, J=8.1 Hz), 7.28–7.32 (m, 1H), 7.65 (d, 1H, J=1.8 Hz), 8.13 (s, 1H); $^{13}$C NMR (75 MHz) δ 53.72, 101.87, 108.56, 109.67, 110.21, 127.28, 140.80, 147.89, 149.65, 164.26; MS m/z 284 (M$^+$), 288 (M$^+$+2).

EXAMPLE 17

Synthesis of methyl 2-chloro-3-(4-dimethylaminophenyl)prop-2(Z)-enoate

In accordance with the general procedure described in Example 1 above, commercial 4-dimethylaminobenzaldehyde was converted to methyl 2-chloro-3-(4-dimethylaminophenyl)prop-2(Z)-enoate as an oil in the indicated yield for Entry 11 in Table 1.

R$_f$: 0.45 (15% EtOAc in hexane). $^1$H NMR (CDCl$_3$, 300 MHz): δ 3.04 (s, 6H), 3.87 (s, 3H, CO$_2$CH$_3$), 6.68 (d, 2H, J=9.0 Hz), 7.83 (s, 1H), 7.40 (d, 2H, J=9.0 Hz). $^{13}$C NMR (CDCl$_3$, 75 MHz): δ 40.22, 53.29, 111.54, 116.14, 120.76, 133.11, 137.78, 151.70, 164.98. MS: m/z 239 (M$^+$), 241 (M$^+$+2).

EXAMPLE 18

Synthesis of methyl 2-chloro-3-(1H-indol-2-yl)prop-2(Z)-enoate

In accordance with the general procedure described in Example 1 above, commercial indole aldehyde was converted to methyl 2-chloro-3-(1H-indol-2-yl)prop-2(Z)-enoate as an oil in the indicated yield for Entry 12 in Table 1.

R$_f$: 0.35 (15% EtOAc in hexane). $^1$H NMR (CDCl$_3$, 300 MHz): δ 3.92 (s, 3H,—CO$_2$CH$_3$), 7.20–7.36 (m, 2H), 7.44 (d, 1H, J=7.2 Hz), 7.81 (d, 1H, J=7.5 Hz), 8.31 (s, 1H), 8.32 (d, 1H, J=4.2 Hz), 8.81 (bs, 1H). $^{13}$C NMR (CDCl$_3$, 75 MHz): δ 53.30,110.97,111.79,117.20,118.60,121.59,123.67, 127.77, 128.76, 129.46, 135.43, 164.67. MS: m/z 235 (M$^+$), 237 (M$^+$+2).

EXAMPLE 19

Synthesis of methyl 2-chloro-3-methyl-undec-2-enoate

In accordance with the general procedure described in Example 3 above, commercial ketone was converted to methyl 2-chloro-3-methyl-undec-2-enoate and as a colorless liquid in the indicated yield for Entry 1 in Table 2.

R$_f$: 0.77 (15% EtOAc in hexane). $^1$H NMR (CDCl$_3$, 300 MHz):(Major isomer)(AK-I-208-18): δ 0.88 (t, 3H, J=6.9 Hz), 1.24–1.34 (m, 10H), 1.43–1.51 (m, 2H), 2.10 (s, 3H,—CH3), 2.50–2.55(m, 2H), 3.80 (s, 3H, CO$_2$CH$_3$). $^{13}$C NMR (CDCl$_3$, 75 MHz): δ 14.30, 22.66, 22.86, 28.38, 29.42, 29.58, 29.77, 32.06, 36.19, 52.65, 118.22, 151.75, 164.07. MS: m/z 246 (M$^+$), 248 (M$^+$+2). $^1$H NMR (CDCl$_3$, 300 MHz):(Minor isomer)(AK-I-208–20): δ 0.88 (t, 3H, J=6.9 Hz), 1.24–1.26 (m, 10H), 1.43–1.53 (m, 2H), 2.15 (s, 3H,—CH$_3$), 2.34–2.39 (m, 2H), 3.80 (s, 3H, CO$_2$CH$_3$). $^{13}$C NMR (CDCl$_3$, 75 MHz): δ 14.29, 21.22, 22.85, 26.81, 29.38, 29.57, 29.75, 32.05, 38.10, 52.66, 117.74, 151.80, 164.07. MS: m/z 246 (M$^+$), 248 (M$^+$+2).

EXAMPLE 20

Synthesis of methyl 2-chloro-3-phenyl-but-2-enoate

In accordance with the general procedure described in Example 3 above, commercial acetophenone was converted to methyl 2-chloro-3-phenyl-but-2-enoate as a colorless liquid in the indicated yield for Entry 2 in Table 2.

R$_f$: 0.65 (15% EtOAc in hexane). $^1$H NMR (CDCl$_3$, 300 MHz):(Major isomer): δ 2.29 (s, 3H,—CH3), 3.53 (s, 3H, CO$_2$CH$_3$), 7.14–7.17 (m, 2H), 7.30–7.40 (m, 3H). $^{13}$C NMR (CDCl$_3$, 75 MHz): δ 23.84, 52.64, 120.00, 126.91, 128.21, 128.47, 141.05, 146.38, 164.69. MS: m/z 210 (M$^+$), 212 (M$^+$+2). $^1$H NMR (CDCl$_3$, 300 MHz):(Minor isomer): δ 2.42 (s, 3H,—CH$_3$), 3.87 (s, 3H, CO$_2$CH$_3$), 7.14–7.17 (m, 2H), 7.30–7.40 (m, 3H). $^{13}$C NMR (CDCl$_3$, 75 MHz): δ 23.71, 52.96, 120.00, 127.16, 128.17, 128.53, 141.05, 146.38, 164.69. MS: m/z 210 (M$^+$), 212 (M$^+$+2).

EXAMPLE 21

Synthesis of methyl 2-chloro-3-cyclohex-1-enyl-but-2-enoate

In accordance with the general procedure described in Example 3 above, commercial ketone was converted to methyl 2-chloro-3-cyclohex-1-enyl-but-2-enoate as an oil in the indicated yield for Entry 3 in Table 2.

R$_f$: 0.71 (15% EtOAc in hexane). $^1$H NMR (CDCl$_3$, 300 MHz):( Major isomer): δ 1.56–1.75 (m,4H), 1.98 (s, 3H,—CH$_3$), 2.00–2.12 (m, 4H), 3.73 (s, 3H, CO$_2$CH$_3$), 5.43–5.46 (m, 1H). $^1$H NMR (CDCl$_3$, 300 MHz):(Minor isomer): δ 1.56–1.75 (m, 4H), 2.00–2.12 (m, 4H), 2.18 (s, 3H,—CH$_3$) 3.82 (s, 3H, CO$_2$CH$_3$), 5.49–5.52 (m, 1H).

EXAMPLE 22

Synthesis of methyl 2-chloro-3-methyl-5-(2,6,6-trimethyl-cyclohex-2-Enyl)-penta-2,4-dienoate In accordance with the general procedure described in Example 3 above, commercial α-ionone was converted to methyl 2-chloro-3-methyl-5-(2,6,6-trimethyl-cyclohex-2-enyl)-penta-2,4-dienoate as a colorless liquid in the indicated yield for Entry 4 in Table 2.

$R_f$: 0.71 (15% EtOAc in hexane). $^1$H NMR (CDCl$_3$, 300 MHz):(Major isomer): δ 0.82 (s, 3H,—CH$_3$), 0.91 (s, 3H, —CH$_3$), 1.17–1.24 (m, 2H), 1.39–1.49 (m, 1H), 1.58–1.59 (m, 3H), 2.00–2.06 (m, 2H), 2.14 (s, 3H), 2.25 (d, 1H, J=9.6 Hz), 3.83 (s, 3H, CO$_2$CH$_3$), 5.44 (br s, 1H), 5.90 (dd, 1H, J=9.6, 15.6 Hz), 7.10 (d, 1H, J=15.6 Hz). $^{13}$C NMR (CDCl$_3$, 75 MHz): δ 18.22, 23.07, 23.27, 27.97, 31.78, 32.66, 52.82, 55.25, 119.82, 121.72, 129.04, 133.67, 139.16, 144.94, 164.25. MS: m/z 282 (M$^+$), 284 (M$^+$+2). $^1$H NMR (CDCl$_3$, 300 MHz):(Minor isomer): δ 0.82 (s, 3H,—CH$_3$), 0.92 (s, 3H,—CH$_3$), 1.18–1.27 (m, 2H), 1.40–1.51 (m, 1H), 1.56–1.61 (m, 3H), 2.00–2.08 (m, 2H), 2.22 (s, 3H), 2.31 (d, 1H, J=9.6 Hz), 3.83 (s, 3H, CO$_2$CH$_3$), 5.46 (br s, 1H), 6.00 (dd, 1H, J=9.6, 15.6 Hz), 6.77 (d, 1H, J=15.6 Hz).

EXAMPLE 23

Synthesis of methyl 2,2-dichloro-3-hydroxy-3-phenylpropenoate

In accordance with the general procedure described in Example 4 above, commercial benzaldehyde was converted to methyl 2,2-dichloro-3-hydroxy-3-phenylpropenoate in the indicated yield for Entry 1 in Table 3.

Mp 63–64° C.; $^1$H NMR (CDCl$_3$, 300 MHz): δ 3.50 (d, 1H, J=5.4 Hz), 3.85 (s, 3H), 5.38 (d, 1H, J=5.4 Hz), 7.33–7.38 (m, 3H), 7.47–7.51 (m, 2H); $^{13}$C NMR (CDCl$_3$, 75 MHz) d 54.77, 78.82, 86.14, 127.93, 128.93, 129.29, 135.55, 166.62.

EXAMPLE 24

Synthesis of methyl 2,2-dibromo-3-hydroxy-3-phenylpropanoate

In accordance with the general procedure described in Example 4 above, commercial benzaldehyde was converted to methyl 2,2-dibromo-3-hydroxy-3-phenylpropanoate in the indicated yield for Entry 2 in Table 3.

$R_f$: 0.44 (30% EtOAc in hexane); mp 58–60° C.; $^1$H NMR (300 MHz) δ 3.45 (d, 1H, J=4.8 Hz), 3.83 (s, 3H), 5.25 (d, 1H, J=4.8 Hz), 7.27–7.32 (m, 3H), 7.49–7.53 (m, 2H); $^{13}$C NMR (75 MHz) δ 54.97, 65.30, 78.92, 127.82, 129.30, 129.33, 136.28, 167.36; MS m/z 336 (M$^+$), 338 (M$^+$+2), 340 (M$^+$+4); HRMS (CI, CH$_4$) calculated for C$_{10}$H$_{11}$Br$_2$O$_3$ (M$^+$+1) m/z 336.9075, found 336.9077.

EXAMPLE 25

Synthesis of methyl 2,2-dichloro-3-hydroxy-5-phenylpentanoate

In accordance with the general procedure described in Example 4 above, commercial aliphatic aldehyde was converted to methyl 2,2-dichloro-3-hydroxy-5-phenylpentanoate in the indicated yield for Entry 3 in Table 3.

$R_f$: 0.26 (20% EtOAc in hexane); mp 53–54° C.; 1H NMR (400 MHz) δ 1.91–2.01 (m, 1H), 2.16–2.24 (m, 1H), 2.66 (d, 1H, J=6.4 Hz), 2.71–2.78 (m, 1H), 2.94–3.01 (m, 1H), 3.88 (s, 3H), 4.19–4.23 (m, 1H), 7.21–7.32 (m, 5H); $^{13}$C NMR (75 MHz) δ 32.00, 32.76, 54.73, 76.68, 86.65, 126.37, 128.67, 128.72, 141.14, 166.56; MS m/z 276 (M$^+$), 278 (M$^+$+2), 230 (M$^+$+4); HRMS (CI, CH$_4$) calculated for C$_{12}$H$_{15}$Cl$_2$O$_3$ (M$^+$+1) m/z 277.0398, found 277.0392.

EXAMPLE 26

Synthesis of methyl 2,2-dichloro-3-hydroxy-5-phenylpent-4(E)-enoate

In accordance with the general procedure described in Example 4 above, commercial cinnamaldehyde was converted to methyl 2,2-dichloro-3-hydroxy-5-phenylpent-4(E)-enoate in the indicated yield for Entry 4 in Table 3.

$R_f$: 0.27 (20% EtOAc in hexane); mp 45–47° C.; $^1$H NMR (400 MHz) δ 2.90 (d, 1H, J=6.6 Hz), 3.92 (s, 3H), 4.96 (t, 1H, J=6.0 Hz), 6.35 (dd, 1H, J=15.6, 6.3 Hz), 6.82 (d, 1H, J=15.6 Hz), 7.28–7.44 (m, 5H); $^{13}$C NMR (75 MHz) δ 54.84, 78.31, 85.88, 123.24, 127.08, 128.70, 128.88, 135.96, 136.31, 166.27; MS m/z 274 (M$^+$), 276 (M$^+$+2), 278 (M$^+$+4); HRMS (CI, CH$_4$) calculated for C$_{12}$H$_{13}$Cl$_2$O$_3$ (M$^+$+1) m/z 275.0242, found 275.0245.

EXAMPLE 27

Synthesis of methyl 2,2-dichloro-3-(2,2-dimethyl-[1,3]dioxolan-4(R)-yl)-3-hydroxypropanoate In accordance with the general procedure described in Example 4 above, commercial chiral glyceraldehyde was converted to methyl 2,2-dichloro-3-(2,2-dimethyl-[1,3]dioxolan-4(R)-yl)-3-hydroxypropanoate in the indicated yield for Entry 5 in Table 3.

Major isomer: $R_f$: 0.70 (50% EtOAc in hexane); mp 102–103° C.; $^1$H NMR (400 MHz) δ 1.30 (s, 3H), 1.35 (s, 3H), 3.09 (d, 1H, J=5.1 Hz), 3.86 (s, 3H), 4.07–4.18 (m, 2H), 4.24–4.33 (m, 2H); $^{13}$C NMR (75 MHz) δ 25.05, 26.25, 54.61, 66.80, 75.36, 78.00, 87.05, 110.14, 165.59; HRMS (CI, CH$_4$) calculated for C$_9$H$_{15}$Cl$_2$O$_5$ (M$^+$+1) m/z 273.0296, found 273.0297. Minor isomer: $R_f$: 0.77 (50% EA in hexane); mp 34–35° C.; $^1$H NMR (400 MHz) δ 1.39 (s, 3H), 1.42 (s, 3H), 3.42 (d, 1H, J=9.3 Hz), 3.85–3.91 (m, 4H), 4.16–4.22 (m, 2H), 4.51–4.56 (m, 1H); $^{13}$C NMR (75 MHz) δ 25.83, 26.17, 54.82, 68.07, 72.94, 76.18, 84.89, 110.71, 165.64; MS m/z 272 (M$^+$), 274 (M$^+$+2), 276 (M$^+$+4); HRMS (CI, CH$_4$) calculated for C$_9$H$_{15}$Cl$_2$O$_5$ (M$^+$+1) m/z 273.0296, found 273.0299.

EXAMPLE 28

Synthesis of ethyl 2,2-difluoro-3-hydroxy-5-phenylpentanoate

In accordance with the general procedure described in Example 4 above, hydrocinnamaldehyde and ethyl difluorobromoacetate were converted to ethyl 2,2-difluoro-3-hydroxy-5-phenylpentanoate in the indicated yield for Entry 6 in Table 3.

$^1$H NMR (CDCl$_3$, 300 MHz): δ 1.27 (t, 3H, J=7.2 Hz), 1.75–2.00 (m, 2H), 2.10 (d, 1H, J=6.9 Hz), 2.61–2.71 (m, 1H), 2.81–2.91 (m, 1H), 3.88–4.02 (m, 1H), 4.26 (q, 2H, J=7.2 Hz), 7.10–7.27 (m, 5H). $^{13}$C NMR (CDCl$_3$, 75 MHz): d 14.13, 30.91, 31.39, 63.32, 70.81, 71.17, 71.50, 126.45, 128.68, 128.78, 140.94.

EXAMPLE 29

Synthesis of 2-chloro-3-phenyl-prop-2(Z)-enamide

In accordance with the general procedure described in Example 1 above, benzaldehyde and commercial 2,2,2-trichloroacetamide were converted to 2-chloro-3-phenyl-acrylamide as a colorless liquid in the indicated yield for Entry 1 in Table 4. Its spectral data were in agreement with values found in the literature. See Kruper, William J., Jr. and Emmons, Albert H., *J. Org. Chem.*, 56: 3323–29 (1991).

EXAMPLE 30

Synthesis of 2-chloro-3-phenyl-pent-2(Z)-enamide

In accordance with the general procedure described in Example 1 above, hydrocinnamaldehyde and commercial 2,2,2-trichloroacetamide were converted to 2-chloro-3-phenyl-pent-2(Z)-enamide in the indicated yield for Entry 2 in Table 4.

$R_f$: 0.20 (30% EtOAc in hexane); $^1$H NMR (CDCl$_3$, 400 MHz) δ 2.58 (q, 2H, J=7.3 Hz), 3.81 (t, 2H, J=7.3 Hz), 5.63 (bs, 1H), 6.46 (bs, 1H), 7.16–7.38 (m, 6H).

EXAMPLE 31

Synthesis of α-chloro-(Z)-stilbene

In accordance with the general procedure described in Example 1 above, benzaldehyde and commercial 1,1,1-trichlorotoluene were converted to α-chloro-(Z)-stilbene in the indicated yield for Entry 3 in Table 4. Its spectral data were in agreement with values found in the literature. See Kokubo et al., *J. Org. Chem.*, 61: 6941–46 (1996).

EXAMPLE 32

Synthesis of 1-chloro-1,4-diphenyl-1(Z)-butene

In accordance with the general procedure described in Example 1 above, hydrocinnamaldehyde and commercial 1,1,1-trichlorotoluene were converted to 1-chloro-1,4-diphenyl-1(Z)-butene in the indicated yield for Entry 4 in Table 4. Its spectral data were in agreement with values found in the literature. See Reich et al., *J. Org. Chem.*, 43: 2402–10 (1978).

EXAMPLE 33

Synthesis of 3-chloro-4-phenyl-but-3(Z)-en-2-one

In accordance with the general procedure described in Example 1 above, benzaldehyde and commercial 1,1,1-trichloroacetone were converted to 3-Chloro-4-phenyl-but-3(Z)-en-2-one in the indicated yield for Entry 5 in Table 4. Its spectral data were in agreement with values found in the literature. See Schlosser, M. and Christmann, K. F., *Synthesis*, 1:38–39 (1969).

EXAMPLE 34

Synthesis of 3-chloro-6-phenyl-hex-3(Z)-en-2-one

In accordance with the general procedure described in Example 1 above, hydrocinnamaldehyde and commercial 1,1,1-trichloroacetone were converted to 3-chloro-6-phenyl-hex-3(Z)-en-2-one in the indicated yield for Entry 6 in Table 4. Its spectral data were in agreement with values found in the literature. See Satoh et al., *Tetrahedron Letters*, 33: 1483–84 (1992).

EXAMPLE 35

Synthesis of 2-methyl-1,3-diphenyl-2(E)-propen-1-one

In accordance with the general procedure described in Example 1 above, benzaldehyde and commercial α,α,-dichloropropiophenone were converted to 2-methyl-1,3-diphenyl-2(E)-propen-1-one in the indicated yield for Entry 7 in Table 4. Its spectral data were in agreement with values found in the literature. See Aoki et al., *Synlett*, 10: 1071–72 (1995).

EXAMPLE 36

Synthesis of 2-methyl-1,5-diphenyl-pent-2(E)-en-1-one

In accordance with the general procedure described in Example 1 above, hydrocinnamaldehyde and commercial α,α,-dichloropropiophenone were converted to 2-Methyl-1,5-diphenyl-pent-2(E)-en-1-one in the indicated yield for Entry 8 in Table 4. Its spectral data were in agreement with values found in the literature. See Ishihara et al., *Synlett*, 5: 597–99 (1997).

What is claimed is:

1. A method for the synthesis of a stereospecific tri-substituted olefin, comprising: reacting an aldehyde substrate with a halogenated compound and 4 equivalents of CrCl$_2$ in a solvent under an inert atmosphere for a sufficient amount of time, wherein the aldehyde substrate is selected from the group consisting of hydrocinnamaldehyde, cinnamaldehyde, chiral glyceraldehyde, 3-bromo-benzaldehyde, p-trifluoromethylbenzaldehyde, p-methoxybenzaldehyde, 4-benzyloxy-3-methoxy-benzaldehyde, 4-dimethylaminobenzaldehyde, and indole aldehyde.

2. The method of claim 1, wherein the halogenated compound is a dihalogenated propionate.

3. The method of claim 2, wherein the dihalogenated propionate is α,α-dichloropropiophenone or methyl 2,2-dichloropropionate.

4. The method of claim 1, wherein the halogenated compound is a trihalogenated compound.

5. The method of claim 4, wherein the trihalogenated compound is selected from the group consisting of methyl trichloroacetate, methyl tribromoacetate, 2,2,2-trichloroacetamide, 1,1,1-trichlorotoluene, 1,1,1-trichloroacetone, and ethyl dibromofluoroacetate.

6. A method for the synthesis of stereospecific tri-substituted olefins, comprising: reacting an aldehyde substrate with a halogenated compound, catalytic chromium, Mn, and TMSCl in a solvent under an inert atmosphere for a sufficient amount of time.

7. The method of claim 6, wherein the aldehyde substrate is selected from the group consisting of aliphatic aldehyde, aryl aldehyde, cycloaliphatic aldehyde, and heteroaromatic aldehyde.

8. The method of claim 6, wherein the aldehyde substrate is selected from the group consisting of hydrocinnamaldehyde, cinnamaldehyde, chiral glyceraldehyde, 3-bromo-benzaldehyde, p-trifluoromethylbenzaldehyde, p-methoxybenzaldehyde, 4-benzyloxy-3-methoxy-benzaldehyde, 4-dimethylaminobenzaldehyde, and indole aldehyde.

9. The method of claim 6, wherein the halogenated compound is a dihalogenated propionate.

10. The method of claim 9, wherein the dihalogenated propionate is α,α-dichloropropiophenone or methyl 2,2-dichloropropionate.

11. The method of claim 6, wherein the halogenated compound is a trihalogenated compound.

12. The method of claim 11, wherein the trihalogenated compound is selected from the group consisting of methyl trichloroacetate, methyl tribromoacetate, 2,2,2-trichloroacetamide, 1,1,1-trichlorotoluene, 1,1,1-trichloroacetone, and ethyl difluorobromoacetate.

13. The method of claim 6, wherein the catalytic chromium is anhydrous $CrCl_2$ at 50 mol % concentration.

14. The method of claim 6, wherein the solvent is THF, DME, or a mixture thereof.

15. The method of claim 6, wherein the synthesis takes place at room temperature.

16. The method of claim 6, wherein the inert atmosphere is an argon atmosphere or a nitrogen atmosphere.

17. The method of claim 6, wherein the amount of time is about 12 hours.

18. A method for the synthesis of a stereospecific tri-substituted olefin, comprising: reacting an aldehyde substrate with a dihalogenated compound, wherein the dihalogenated compound is dihalogenated propionate or a homolog of dihalogenated propionate with a longer carbon chain, and 4 equivalents of $CrCl_2$ in a solvent under an argon atmosphere for about 0.5 hours.

19. A method for the synthesis of stereospecific tetra-substituted olefins, comprising: reacting a ketone substrate with a trihalogenated compound and 4 equivalents of $CrCl_2$ in a solvent under an inert atmosphere for a sufficient amount of time.

20. The method of claim 19, wherein the ketone substrate is selected from the group consisting of aliphatic ketone, aromatic ketone, conjugated ketone, and hindered ketone.

21. The method of claim 19, wherein the ketone substrate is acetophenone or α-ionone.

22. The method of claim 19, wherein the trihalogenated compound is methyl trichloroacetate or methyl tribromoacetate.

23. The method of claim 19, wherein the solvent is selected from the group consisting of THF, DMF, DME, and a mixture thereof.

24. The method of claim 19, wherein the synthesis takes place at room temperature.

25. The method of claim 19, wherein the inert atmosphere is an argon atmosphere or a nitrogen atmosphere.

26. The method of claim 19, wherein the amount of time is about 2 hours.

27. A method for the synthesis of dihalohydrins, comprising: reacting a substrate, wherein the substrate is an aldehyde or a ketone, and a trihalogenated compound with 2 equivalents of $CrCl_2$ in a solvent under an inert atmosphere for a sufficient amount of time.

28. The method of claim 27, wherein the substrate is selected from the group consisting of aliphatic aldehyde, aryl aldehyde, cycloaliphatic aldehyde, and heteroaromatic aldehyde.

29. The method of claim 27, wherein the trihalogenated compound is methyl trichloroacetate, methyl tribromoacetate, or ethyl difluorobromoacetate.

30. The method of claim 27, wherein the solvent is THF, DME, or a mixture thereof.

31. The method of claim 27, wherein the synthesis takes place at about 0° C.

32. The method of claim 27, wherein the inert atmosphere is an argon atmosphere or a nitrogen atmosphere.

33. The method of claim 27, wherein the amount of time is about 6 hours.

* * * * *